United States Patent [19]

Yamanishi et al.

[11] Patent Number: 4,622,296
[45] Date of Patent: Nov. 11, 1986

[54] PROCESS FOR MEASURING ACTIVITY OF DEHYDROGENASE EMPLOYING A REACTION STOPPER

[75] Inventors: Kazuhiko Yamanishi, Tokyo; Toshiro Hanada, Kawagoe, both of Japan

[73] Assignee: Wako Pure Chemical Industries, Ltd., Osaka, Japan

[21] Appl. No.: 686,817

[22] Filed: Dec. 27, 1984

[30] Foreign Application Priority Data

Dec. 28, 1983 [JP] Japan ............................... 58-251883

[51] Int. Cl.$^4$ ........................................... C12Q 1/32
[52] U.S. Cl. ..................................... 435/26; 435/184
[58] Field of Search .................................. 435/26, 184

[56] References Cited

U.S. PATENT DOCUMENTS 3,893,890 7/1975 Wurzburg et al. .................. 435/184
3,985,621 10/1976 Maruyama et al. .................. 435/184

FOREIGN PATENT DOCUMENTS 0037742 10/1981 European Pat. Off. .............. 435/26

*Primary Examiner*—Sam Rosen
*Assistant Examiner*—William J. Herald
*Attorney, Agent, or Firm*—Armstrong, Nikaido, Marmelstein & Kubovcik

[57] ABSTRACT

In a process for measuring the activity of a dehydrogenase or the amount of substrate reacted in the presence of the dehydrogenase using NAD or NADP as coenzyme and a tetrazolium salt as a color-producing reagent, when at least one member selected from the group consisting of dodecyl sulfate, decyl sulfate, dodecylbenzenesulfonic acid, and salts thereof is used as a reaction stopper, resulting in enhancement of coloring, stability of the produced color and prevention of the produced formazan compound from staining the laboratoryware.

20 Claims, No Drawings

PROCESS FOR MEASURING ACTIVITY OF DEHYDROGENASE EMPLOYING A REACTION STOPPER

BACKGROUND OF THE INVENTION

This invention relates to a process for measuring the activity of a dehydrogenase and a process for determining the amount of a substrate using a dehydrogenase acting specifically thereupon.

The activity of dehydrogenases such as lactate dehydrogenase (hereinafter referred to as "LDH"), glucose-6-phosphate dehydrogenase, glycerol-3-phosphate dehydrogenase, α-hydroxybutyrate dehydrogenase (hereinafter referred to as "α-HBD"), a 3α-hydroxysteroid dehydrogenase (hereinafter referred to as "3α-HSD"), etc., using nicotinamide adenine dinucleotide (NAD) or nicotinamide adenine dinucleotidephosphate (NADP) as hydrogen acceptor can be measured by a UV method or a visible colorimetric method. According to the UV method, the increase in absorbance due to NADH (nicotinamide adenine dinucleotide, reduced form) or NADPH (nicotinamide adenine dinucleotidephosphate, reduced form) produced by the enzymatic reaction of a substrate and a dehydrogenase is usually measured at 340 nm in a certain time period (employing a so-called rate assay).

According to the visible colorimetric method, the produced NADH or NADPH reduces a tetrazolium salt with the aid of an electron carrier or diaphorase to produce a formazan dye, the color of which is measured colorimetrically. The principle of the visible colorimetric method, for example, in the measurement of the activity of LDH can be shown as follows:

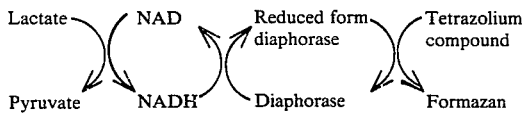

Since these reactions proceed quantitatively and specifically, the activity of LDH can be measured by measuring quantitatively the color concentration of the formazan produced. Generally speaking, the visible colorimetric method comprises conducting an enzymatic reaction in a certain number of minutes, adding an enzymatic reaction stopper to the reaction system to stop the reaction, and measuring the amount of dye corresponding to the amount of NADH produced colorimetrically.

As a method for stopping the reaction, there is most popularly employed a method wherein the enzymatic reaction is stopped by making the reaction solution strongly acidic. As the acidifying agent, there is generally used an inorganic acid such as hydrochloric acid. But the use of such an inorganic acid produces various disadvantages in that the formazan (or diformazan) dye produced is easily faded when exposed to light, some formazans produce clouding or precipitation due to low solubility, staining of test tubes and cuvettes takes place thus causing errors in measurement, a large specimen blank value due to clouding is obtained in the case of using chyle serum as specimen, which cause errors in ordinary examinations wherein no specimen blank is taken, and the like. Therefore, elimination of such disadvantages has been desired.

SUMMARY OF THE INVENTION

It is an object of this invention to provide a process for measuring the activity of a dehydrogenase or the amount of a substrate using a dehydrogenase, without the disadvantages of the visible colorimetric method.

This invention provides a process for measuring the activity of a dehydrogenase comprising conducting an enzymatic reaction of a dehydrogenase in the presence of NAD or NADP as coenzyme, and a tetrazolium salt as a color-producing reagent, stopping the reaction by adding an enzymatic reaction stopper thereto, and measuring colorimetrically the activity of dehydrogenase, characterized in that the stopper is at least one member selected from the group consisting of decyl sulfate and salts thereof, dodecyl sulfate and salts thereof, dodecylbenzenesulfonic acid and salts thereof.

This invention also provides a process for determining the amount of a substrate comprising reacting a substrate in the presence of a dehydrogenase in a predetermined time period using NAD or NADP as coenzyme and a tetrazolium salt as a color-producing reagent, stopping the reaction by adding an enzymatic reaction stopper thereto, and determining colorimetrically the amount of the substrate, characterized in that the stopper is at least one member selected from the group consisting of decyl sulfate and salts thereof, dodecyl sulfate and salts thereof, dodecylbenzenesulfonic acid and salts thereof.

DESCRIPTION OF THE PREFERRED EMBODIMENTS

According to the process of this invention, the enzymatic reaction can be stopped completely even in the pH range suitable for the dehydrogenase reaction, and deposition or staining by the formazan or diformazan dye produced can be prevented. Further, it is very surprising that great effects are observed such as improvement of color-producing stability and enhancement of color-production.

The reaction stopper used in this invention not only stops the dehydrogenase reaction caused by the action of dehydrogenase on a substrate, but also inhibits completely the reduction of a tetrazolium salt with a reduced form coenzyme in the presence of an electron carrier or diaphorase. For example, when nitrotetrazolium blue (hereinafter referred to as "Nitro-TB") is added to a buffer solution containing NADH or NADPH and 1-methoxy-PMS or diaphorase, it is immediately reduced to formazan having a violet color. In such a case, when the buffer solution already contains, for example, sodium dodecyl sulfate, color development of Nitro-TB is not observed completely after the addition of Nitro-TB. In this case, when absorbance of NADH or NADPH at 340 nm is traced with the lapse of time without adding Nitro-TB, the absorbance is reduced with the lapse of time and decomposition of NADH or NADPH is observed. This means that sodium dodecyl sulfate inhibits the reduction of Nitro-TB with NADH or NADPH but does not affect the shelf-decomposition of NADH or NADPH.

That is, the reaction stopper used in this invention not only stops the dehydrogenase reaction but also stops the reduction of tetrazolium salt by inhibiting the transfer of electrons to the tetrazolium salt by the electron carrier or diaphorase, but hardly affects the reaction of $$NAD \text{ (or } NADP) \rightleftharpoons NADH \text{ (or } NADPH).$$

Therefore, in order to obtain the produced amount of reduced form coenzyme in a certain period of time using a tetrazolium salt in the presence of an electron carrier or diaphorase in a continuous reaction for producing the reduced form coenzyme, the most effective method is by using the reaction stopper used in this invention. With the reaction stopper used in this invention, the reaction for producing the reduced form coenzyme can be continued, while the reduction of tetrazolium salt (tetrazolium salt→formazan) is completely inhibited, so that further color development does not proceed, which makes it possible to conduct a colorimetric determination and to produce the reduced form coenzyme easily and effectively.

The reaction stopper usable in this invention is at least one member selected from the group consisting of decyl sulfate and salts (e.g. alkali metal (Na, K, Li, etc.) salts) thereof, dodecyl sulfate and salts (e.g. alkali metal (Na, K, Li, etc.) salts) thereof, dodecylbenzenesulfonic acid and salts (e.g. alkali metal (Na, K, Li, etc.) salts) thereof. The concentration of reaction stopper in the final color-developed solution is sufficient if it is 1.5 mmole/liter or more, and preferably in the range of 3 to 100 mmole/liter.

In the colorimetric determination, test tubes and cuvettes are easily stained by the formazan dye produced by the reduction of tetrazolium salt. Such staining can be prevented by the addition of gelatin to the tetrazolium salt-containing solution. However when an acidic stopper solution such as hydrochloric acid solution is used as the reaction stopper as in a known method, gelatin is gradually hydrolyzed. Thus, the use of hydrochloric acid as a stopper is not preferable from the viewpoint of storage for a long period of time.

Such a problem can be solved by the use of the reaction stopper used in this invention. That is, since the reaction stopper solution can be used in near neutral conditions, gelatin does not undergo hydrolysis even if the solution is stored for a long period of time. Thus, when gelatin is added to the enzymatic reaction solution, its effects in preventing deposition and staining of formazan or diformazan can further be enhanced. In such a case the pH of the reaction stopper solution is preferably 6 to 9.

A particularly effective gelatin has a molecular weight of 20,000 to 150,000. However, the gelatin is not particularly limited to such a molecular weight. Any gelatin which has a stain prevention effect can be used in this invention.

Gelatin is usually present in an aqueous or buffer solution. The concentration of gelatin in the solution is usually 0.1 to 0.7 weight/volume (W/V) %, preferably 0.2 to 0.5 W/V %.

This invention can be applied to various measuring processes such as the determination of enzyme activities, and determination of substrates, relying on the reaction wherein NAD or NADP is used as coenzyme, and a substrate is reacted in the presence of a dehydrogenase to produce NADH or NADPH, which reduces a tetrazolium salt in the presence of an electron carrier or diaphorase to yield a formazan compound.

Typical examples are processes for determining the amount of substrates using dehydrogenases or the activity of dehydrogenases in test samples wherein the substrates or dehydrogenases are components of body fluid.

Examples of the substrates are lactic acid, α-hydroxybutyric acid, cholesterol, bile acids, glycerol, glycerol-3-phosphate, glucose-6-phosphate, formaldehyde, acetoaldehyde, alcohols, etc.

Examples of the dehydrogenases are lactate dehydrogenase (LDH), α-hydroxybutyrate dehydrogenase (α-HBD), cholesterol dehydrogenase, 3α-hydroxysteroid dehydrogenase (3α-HSD), glycerol-3-phosphate dehydrogenase, glucose-6-phosphate dehydrogenase, formaldehyde dehydrogenase, aldehyde dehydrogenase, alcohol dehydrogenase, etc.

The electron carrier or diaphorase is usually used in the reaction wherein a formazan compound is produced by the reduction of a tetrazolium salt with a reduced form coenzyme.

Examples of the electron carrier are phenazine methosulfate (PMS), 1-methoxyphenazine methosulfate (1-methoxy-PMS), 9-dimethylaminobenzo-α-phenazoxonium chloride (Meldola's Blue), etc.

Examples of the tetrazolium compound are 3-(p-iodophenyl)-2-(p-nitrophenyl)-5-phenyl-2H tetrazolium chloride (INT), 3-(4,5-dimethyl-2-thiazolyl)-2,5-diphenyl-2H tetrazolium bromide (MTT), 3,3'-(4,4'-biphenylylene)-bis(2,5-diphenyl-2H tetrazolium chloride) (Neo-TB), 3,3'-(3,3'-dimethoxy-4,4'-biphenylylene)-bis[2-(p-nitrophenyl)-5-phenyl-2H tetrazolium chloride] (Nitro-TB), 3,3'-(3,3'-dimethoxy-4,4'-biphenylylene)-bis(2,5-diphenyl-2H tetrazolium chloride) (TB), 3,3'-(3,3'-dimethoxy-4,4'-biphenylylene)-bis[2,5-bis(p-nitrophenyl)-2H tetrazolium chloride] (TNTB), water-soluble tetrazolium salts such as 2-(2-benzothiazolyl)-3-(o-carboxyphenyl)-5-[p-{hydroxy-poly(oxy-1,2-ethanediyl)}phenyl]-2H tetrazolium chloride, etc.

According to the present invention, the formazan dye produced by the reduction of tetrazolium salt can effectively be prevented from depositing and staining, color-producing stability is improved and color-production can be improved by the use of at least one member selected from the group consisting of decyl sulfate and salts thereof, dodecyl sulfate and salts thereof, dodecylbenzenesulfonic acid and salts thereof as the reaction stopper in the measurement of activity of the dehydrogenases and the determination of substrates using dehydrogenases, using NAD or NADP as a coenzyme and a tetrazolium salt as color-producing reagent.

This invention is illustrated by way of the following Examples.

EXAMPLE 1

Measurement of Activity of Lactate Dehydrogenase in Serum

A substrate solution was prepared by dissolving the following ingredients in 0.1M tris-HCl buffer solution (pH 8.3):

lithium DL-lactate: 0.1 mole/l.
NAD: 0.2%
diaphorase: 200 units/dl.
Nitro-TB: 0.02%

A 0.3% sodium dodecyl sulfate (SDS) aqueous solution was prepared as a reaction stopper.

To a 0.5 ml of the substrate solution pre-heated at 37° C., 0.05 ml of serum was added and the resulting solution incubated at 37° C. for precisely 10 minutes. Then, 5.0 ml of the reaction stopper was added to the reaction solution and mixed.

Absorbance at 560 nm was measured using a reagent blank as control. By comparison with calibration curves obtained by using standard serum (activity of LDH being known) in the same manner as described above, the activity of LDH in the serum was measured. When 5 ml of 0.1N HCl was used as a reaction stopper in place of the 0.3% sodium dodecyl sulfate aqueous solution according to a conventional process, a glass cell used for determining the absorbance was stained after several tens of samples were measured. In contrast, when the sodium dodecyl sulfate aqueous solution was used, almost no staining of the glass cell was observed after several tens of samples were measured. Further, the effects of this invention were also observed in the degree of color-production and color-producing stability.

Sample blank values when measured with chyle serum in the same manner as mentioned above are shown in the following Table 1.

TABLE 1

| | Process of this invention SDS concentration | | | | Conventional process |
|---|---|---|---|---|---|
| | 0.1% | 0.3% | 0.5% | 1.0% | 0.1 N HCl |
| Absorbance of sample blank | 0.016 | 0.011 | 0.010 | 0.010 | 0.026 |

As is clear from Table 1, the sample blank values of chyle serum according to this invention are ⅔ to ⅓ time less than that of the conventional process.

EXAMPLE 2

Stopping the Reduction Reaction of Tetrazolium Salt by Sodium Dodecyl Sulfate

To 3 ml of 0.1M tris-HCl buffer solution (pH 7.5) containing 0.02% of Nitro-TB, 150 U/dl diaphorase or 0.002% 1-methoxy-PMS, 0.05% of Triton X-100 (octyl phenoxy polyethoxyethanol—available from Rohm and Haas Company), and 0.5% of sodium dodecyl sulfate (SDS), 0.05 ml of 1 mM or 2 mM NADH aqueous solution were added and the resulting solution incubated at 37° C. for 10 minutes. Then, absorbance at 560 nm was measured using a reagent blank as control.

For comparison, the same reagents as mentioned were used except that sodium dodecyl sulfate was not added, the absorbance was measured in the same manner as mentioned above.

The results are shown in the following Table 2.

TABLE 2

| | Diaphorase | | 1-Methoxy-PMS | |
|---|---|---|---|---|
| SDS | None | Yes | None | Yes |
| NADH 1 mM | 0.295 | 0 | 0.289 | 0 |
| NADH 2 mM | 0.587 | 0 | 0.583 | 0 |

As is clear from Table 2, when the reaction stopper in the scope of this invention is used, it completely stops the reduction reaction of the tetrazolium salt by NADH or NADPH with the aid of the electron carrier or diaphorase.

EXAMPLE 3

Measurement of Activity of α-Hydroxybutrate Dehydrogenase in Serum

A substrate solution was prepared by dissolving the following ingredients in 0.1M tris-HCl buffer solution (pH 8.5):

lithium α-hydroxybutyrate: 0.15 mole/l.
NAD: 2 g/l.
PMS: 30 mg/l.
Nitro-TB: 0.8 g/l A 0.3% sodium dodecyl sulfate aqueous solution was prepared as a reaction stopper.

To 0.5 ml of the substrate solution pre-heated at 37° C., 0.05 ml of serum was added and the resulting solution was incubated at 37° C. for precisely 20 minutes. Then, 5.0 ml of the reaction stopper was added to the reaction solution and mixed.

Absorbance at a wavelength of 560 nm was measured using a reagent blank as control. By comparison with calibration curves obtained by using standard serum (activity values of α-HBD being known) in the same manner as described above, the activity of α-HBD in the serum was obtained.

COMPARATIVE EXAMPLE 1

The procedures of Example 3 were repeated to measure the activity of α-HBD in serum except that 0.1N HCl was used as reaction stopper.

The results are shown in the following Table 3.

TABLE 3

| | Standing time | Example 3 | Comparative Example 1 |
|---|---|---|---|
| Absorbance of standard serum | 0 | 0.378 | 0.360 |
| | 3 hrs | 0.378 | 0.345 |
| Absorbance of human serum | 0 | 0.327 | 0.314 |
| | 3 hrs | 0.328 | 0.301 |
| Staining of test tubes | 3 hrs | Almost no staining | Slightly stained |

As is clear from Table 3, when the reaction stopper in the scope of this invention is used, the enzymatic reaction is stopped completely and the degree of coloring is not changed after 3 hours. Further, the degree of coloring of Example 3 is 4 to 5% as high as that of Comparative Example 1 and no staining on the test tubes is observed.

EXAMPLE 4

Measurement of Activity of α-Hydroxybutyrate Dehydrogenase in Serum

Using the same substrate solution and serum sample as used in Example 3 and a 0.3% sodium decyl sulfate aqueous solution as reaction stopper, the activity of α-HBD in serum was measured in the same manner as described in Example 3. The results were the same as those obtained in Example 3.

EXAMPLE 5

Measurement of Activity of LDH in Serum

A substrate solution was prepared by dissolving the following ingredients in 0.1M tris-HCl buffer solution (pH 8.3):

lithium DL-lactate: 0.1 mole/l.
NAD: 0.2%
diaphorase: 200 units/dl
Nitro-TB: 0.02%
gelatin: 0.1%

An aqueous solution containing 0.3% sodium dodecyl sulfate and 0.2% gelatin was prepared as the reaction stopper.

To 0.5 ml of the substrate solution pre-heated at 37° C., 0.05 ml of serum was added and the resulting solution was incubated at 37° C. for precisely 10 minutes.

Then, 5.0 ml of the reaction stopper was added to the reaction solution and mixed.

Absorbance at a wavelength of 560 nm was measured by using a reagent blank as control. By comparison with calibration curves obtained by using standard serum (activity values of LDH being known) in the same manner as described above, the activity of LDH in the serum was obtained.

COMPARATIVE EXAMPLE 2

Using the same substrate solution as used in Example 5, and 0.1N HCl containing 0.2% of gelatin as the reaction stopper, the activity of LDH was measured in the same manner as described in Example 5.

The results of Example 5 and Comparative Example 2 were shown in the following Table 4.

TABLE 4

| | Standing time | Example 5 | Comparative Example 2 |
|---|---|---|---|
| Absorbance of standard serum | 0 | 0.426 | 0.406 |
| | 3 hrs | 0.427 | 0.392 |
| Absorbance of human serum | 0 | 0.241 | 0.232 |
| | 3 hrs | 0.243 | 0.219 |
| Staining of test tubes | 24 hrs | No staining | No staining |

As is clear from Table 4, Example 5 shows an increase of 4 to 5% in the degree of coloring compared with Comparative Example 2. Further, as to the color-producing stability, Example 5 shows no change in absorbance at all after 3 hours, while Comparative Example 2 shows 4 to 5% decrease in the color-production. However, staining of the test tubes is not observed in either of Example 5 and Comparative Example 2 after standing for 24 hours due to the effect of the addition of gelatin.

When the reaction stoppers of Example 5 and Comparative Example 2 which has been stored at room temperature for one month were used in the same manner as described above, staining was observed in the finally colored solution upon standing for 3 days due to hydrolysis of gelatin during the storage in the case of Comparative Example 2, while no staining was even after 3 days in the case of Example 5.

EXAMPLE 6

Measurement of Activity of LDH in Serum

A substrate solution was prepared by dissolving the following ingredients in 0.1M tris-HCl buffer solution (pH 8.3):
lithium DL-lactate: 0.1 mole/l
NAD: 0.2%
diaphorase: 200 units/dl
INT: 0.025%

A 0.1M tris-HCl buffer solution (pH 8.0) containing 1% sodium dodecyl sulfate was prepared as the reaction stopper.

The procedures of Example 5 were repeated for measuring the activity of LDH in serum by using the measuring wavelength of 500 nm.

COMPARATIVE EXAMPLE 3

The activity of LDH was measured in the same manner as described in Example 6 except for using as the reaction stopper 0.1N HCl and the wavelength of 492 nm.

The results of Example 6 and Comparative Example 3 are shown in the following Table 5.

TABLE 5

| | Standing time | Example 6 | Comparative Example 3 |
|---|---|---|---|
| Absorbance of standard serum | 0 | 0.566 | 0.530 |
| | 3 hrs | 0.565 | 0.505 |
| Absorbance of human serum | 0 | 0.325 | 0.306 |
| | 3 hrs | 0.325 | 0.283 |
| Staining of test tubes | 3 hrs | No staining | No staining |

As is clear from Table 5, Example 6 is improved in the degree of coloring by 6 to 7% compared with Comparative Example 3. Further, as to the color-producing stability, Example 6 shows no lowering, while Comparative Example 3 shows 5 to 7% lowering in the color development after standing for 3 hours. Since INT is weaker in staining properties compared with Nitro-TB, no staining is observed in both cases.

The measuring wavelengths are different in Example 6 and Comparative Example 3, since the maximum absorption wavelength which is employed in the both examples is shifted by the addition of sodium dodecyl sulfate.

EXAMPLE 7

Measurement of Activity of LDH in Serum

There were used the same substrate solution and serum sample as used in Example 6 and 0.1M tris-HCl buffer solution (pH 8.0) containing 1% sodium dodecylbenzenesulfonate as the reaction stopper. The procedures of Example 5 were repeated to measure the activity of LDH in the serum. The results were the same as those obtained in Example 6.

EXAMPLE 8

Stabilizing Effect of Sodium Dodecyl Sulfate on Formazan

The stabilizing effect of sodium dodecyl sulfate on dyes at the same pH was examined by reducing three kinds of tetrazolium salts with a predetermined amounts of NADH and 1-methoxy-PMS to form formazan (or diformazan), which was added with or not added with sodium dodecyl sulfate.

As the tetrazolium salts, Nitro-TB, INT and Neo-TB were used in concentration of 0.5 mmole/l in each case dissolved in 0.1M tris-HCl buffer solution (pH 8.0) and 0.02% of Triton X-100 was added to the Nitro-TB and INT solutions, respectively and 0.1% of Triton X-100 was added to the Neo-TB solution, to produce the color-producing reagent solutions.

To 2 ml of the color-producing reagent solution, 50 μl of NADH in concentration of 2.6 mmole/l was added and 1 ml of 0.1M tris-HCl buffer solution (pH 8.0) containing 1.5 mg/dl of 1-methoxy-PMS was added thereto. After incubation at 37° C. for 10 minutes, 2 ml of 0.1M tris-HCl buffer solution (pH 8.0) containing 52 mmole/l of sodium dodecyl sulfate or 2 ml of 0.1M tris-HCl buffer solution (pH 8.0) containing no sodium dodecyl sulfate was added thereto. Absorbances were measured at the maximum absorbance wavelengths, respectively, using a reagent blank as control, followed by measurement of absorbances after further incubation at 37° C. for 2 hours.

The results are shown in Table 6.

TABLE 6

| Tetrazolium salt | Nitro-TB | | Neo-TB | | INT | |
|---|---|---|---|---|---|---|
| Sodium dodecyl sulfate (SDS) | None | Yes | None | Yes | None | Yes |
| Maximum absorption wavelength (nm) | 560 | 560 | 515 | 530 | 492 | 500 |
| Absorbance | | | | | | |
| Immediately after the reaction stoppage | 0.319 | 0.373 | 0.080 | 0.091 | 0.397 | 0.496 |
| After 2 hrs | 0.265 | 0.371 | 0.073 | 0.091 | 0.322 | 0.498 |
| Color retaining rate (%) | 83 | 99 | 91 | 100 | 81 | 100 |
| Color increasing rate (%) | | 16.9 | | 13.8 | | 24.9 |

Note $$\text{Color retaining rate} = \frac{\text{Absorbance after 2 hours}}{\text{Absorbance immediately after reaction stoppage}} \times 100(\%)$$

$$\text{Color increasing rate} = \frac{\text{Absorbance immediately after reaction stoppage by SDS}}{\text{Absorbance immediately after reaction stoppage without SDS}} \times 100 - 100(\%)$$

As is clear from Table 6, remarkable color-producing stability and color-enhancing effects are exhibited by sodium dodecyl sulfate used as the reaction stopper.

What is claimed is:

1. In a process for measuring the activity of a dehydrogenase comprising conducting an enzymatic reaction of a dehydrogenase in the presence of nicotinamide adenine dinucleotide as coenzyme and a tetrazolium salt as a color-producing reagent, stopping the reaction by adding a reaction stopper thereto, and measuring the activity of the dehydrogenase by colorimetic determination, the improvement wherein the reaction stopper is at least one member selected from the group consisting of decyl sulfate and salts thereof, dodecyl sulfate and salts thereof, and dodecylbenzenesulfonic acid and salts thereof.

2. A process according to claim 1, wherein the salts of decyl sulfate, dodecyl sulfate and dodecylbenzenesulfonic acid are alkali metal salts thereof.

3. A process according to claim 1, wherein the reaction stopper is used together with gelatin.

4. A process according to claim 1, wherein the reaction stopper is sodium dodecyl sulfate.

5. A process according to claim 3, wherein the reaction stopper is sodium dodecyl sulfate.

6. In a process for determining the amount of a substrate comprising reacting a substrate in the presence of a dehydrogenase using nicotinamide adenine dinucleotide as coenzyme and a tetrazolium salt as a color-producing reagent, stopping the reaction by adding a reaction stopper thereto, and measuring the amount of substrate by colorimetric determination, the improvement wherein the reaction stopper is at least one member selected from the group consisting of decyl sulfate and salts thereof, dodecyl sulfate and salts thereof, and dodecylbenzenesulfonic acid and salts thereof.

7. A process according to claim 6, wherein the salts of decyl sulfate, dodecyl sulfate and dodecylbenzenesulfonic acid are alkali metal salts thereof.

8. A process according to claim 6, wherein the reaction stopper is used together with gelatin.

9. A process according to claim 6, wherein the reaction stopper is sodium dodecyl sulfate.

10. A process according to claim 8, wherein the reaction stopper is sodium dodecyl sulfate.

11. In a process for measuring the activity of a dehydrogenase comprising conducting an enzymatic reaction of a dehydrogenase in the presence of nicotinamide adenine dinucleotide phosphate as coenzyme and a tetrazolium salt as a color-producing reagent, stopping the reaction by adding a reaction stopper thereto, and measuring the activity of the dehydrogenase by colorimetric determination, the improvement wherein the reaction stopper is at least one member selected from the group consisting of decyl sulfate and salts thereof, dodecyl sulfate and salts thereof, and dodecylbenzenesulfonic acid and salts thereof.

12. A process according to claim 11, wherein the salts of decyl sulfate, dodecyl sulfate and dodecylbenzenesulfonic acid and alkali metal salts thereof.

13. A process according to claim 11, wherein the reaction stopper is used together with gelatin.

14. A process according to claim 11, wherein the reaction stopper is sodium dodecyl sulfate.

15. A process according to claim 13, wherein the reaction stopper is sodium dodecyl sulfate.

16. In a process for determining the amount of a substrate comprising reacting a substrate in the presence of a dehydrogenase using nicotinamide adenine dinucleotide phosphate as coenzyme and a tetrazolium salt as a color-producing reagent, stopping the reaction by adding a reaction stopper thereto, and measuring the amount of substrate by colorimetric determination, the improvement wherein the reaction stopper is at least one member selected from the group consisting of decyl sulfate and salts thereof, dodecyl sulfate and salts thereof, and dodecylbenzenesulfonic acid and salts thereof.

17. A process according to claim 16, wherein the salts of decyl sulfate, dodecyl sulfate and dodecylbenzenesulfonic acid are alkali metal salts thereof.

18. A process according to claim 16, wherein the reaction stopper is used together with gelatin.

19. A process according to claim 16, wherein the reaction stopper is sodium dodecyl sulfate.

20. A process according to claim 18, wherein the reaction stopper is sodium dodecyl sulfate.

* * * * *